(12) United States Patent
Canuto

(10) Patent No.: US 11,591,220 B2
(45) Date of Patent: Feb. 28, 2023

(54) NANOSTRUCTURED-CARBON-BASE-MATERIAL USING MANTLE PERIDO CARBON MINERALIZATION BASED ACTIVATED CARBON NANOTUBES

(71) Applicant: Teresita Amponin Canuto, Van Nuys, CA (US)

(72) Inventor: Teresita Amponin Canuto, Van Nuys, CA (US)

( * ) Notice: Subject to any disclaimer, the term of this patent is extended or adjusted under 35 U.S.C. 154(b) by 281 days.

(21) Appl. No.: 16/873,848

(22) Filed: Jul. 27, 2020

(65) Prior Publication Data
US 2022/0024767 A1 Jan. 27, 2022

(51) Int. Cl.
| | |
|---|---|
| *C01B 32/16* | (2017.01) |
| *H01M 4/90* | (2006.01) |
| *B01J 20/20* | (2006.01) |
| *B01J 20/30* | (2006.01) |
| *A61K 47/02* | (2006.01) |
| *C12N 5/00* | (2006.01) |

(52) U.S. Cl.
CPC .............. *C01B 32/16* (2017.08); *A61K 47/02* (2013.01); *B01J 20/205* (2013.01); *B01J 20/3021* (2013.01); *B01J 20/3085* (2013.01); *C12N 5/0075* (2013.01); *H01M 4/90* (2013.01); *C12N 2531/00* (2013.01); *C12N 2533/00* (2013.01)

(58) Field of Classification Search
CPC ........ C01B 32/16; A61K 47/02; B01J 20/205; B01J 20/3021; B01J 20/3085; C12N 5/0075; C12N 2531/00; C12N 2533/00; H01M 4/90

USPC ....................................................... 423/447.2
See application file for complete search history.

(56) References Cited

FOREIGN PATENT DOCUMENTS

| CN | 111318257 A | * | 6/2020 | ............ B01J 20/205 |
| WO | WO-2008048247 A2 | * | 4/2008 | ............ B01J 20/205 |

* cited by examiner

*Primary Examiner* — Edward M Johnson
(74) *Attorney, Agent, or Firm* — Bold IP, PLLC; Houda El-Jarrah

(57) ABSTRACT

Mineralization occurs during weathering of silicate materials/rocks rich in CA+ and Mg+, particularly peridotite which composes Earth's upper mantle. The carbon mineralization mantle peridotite is the base activated carbon for nanostructured-carbon-base-material. The nanostructured-carbon-base-material using mantle peridotite carbon mineralization based activated carbon nanotubes is a new catalyst for batteries and fuel-cell use that doesn't use precious metal such as platinum and that performs as effectively as many well-known, expensive precious-metal catalysts. The nanostructured-carbon-base-material using mantle peridotite carbon mineralization based activated carbon nanotubes makes possible the creation of economical lithium-air batteries that could power electric vehicles. The carbon nanotubes have useful qualities such as slim, strong, lightweight, high electronic conductivity, has metallic/semiconductive properties that are useful in (1) electronics i.e. wiring, transistor; (2) material that reinforced resin/metal; (3) energy source i.e. catalysis support, ion adsorption, capacitors; (4) nanotechnology i.e. nanostructure; and (5) biotechnology i.e. cell cultivating, drug delivery system, biosensor.

3 Claims, 8 Drawing Sheets

NANOSTRUCTURED-CARBON-BASE-MATERIAL USING MANTLE PERIDO CARBON MINERALIZATION BASED ACTIVATED CARBON NANOTUBES

BACKGROUND OF THE INVENTION

The present invention relates to economical non-precious metal catalyst of lithium-air batteries. The new catalyst doesn't use precious metal such as platinum, which is more expensive per ounce than gold. Yet it performs under certain conditions as effectively as many well-known and prohibitively expensive precious metal catalyst developed for battery and fuel-cell use. The catalyst is based on nitrogen-containing carbon nanotubes, it does not require the tedious, toxic and costly nanotechnology materials.

Carbon nanotubes for better and low cost electrodes for fuel cells, carbon nanotubes to epoxy composites in stronger/stiffer components of windmill blades or aircraft components, carbon nanotubes in ink, carbon fibers (baseball bats, golf clubs, airplane body, car panels, any situation where metal can be replaced by carbon fiber), carbon fiber tapes, tow and sleeves, carbon fabrics (twill), carbon fiber reinforce plastics or thermoplastic, carbon nanotubes for computer chips, carbon nanotubes mirrors for lightweight telescopes in cube sats.

The composition of carbon nanotubes is from the carbon mineralization mantle peridotite. The peridotite carbon mineralization is the product of air pollution treatment that target pollutants such as carbon dioxide ($CO_2$) in air using the highly reactive rock fragments of peridotite that is rich in Mg and Ca and the product of $CO_2$ sequestration in using the peridotite glass cells is natural carbon. The carbon mineralization mantle peridotite is the peridotite carbon mineralization based is then the based activated carbon nanotubes.

SUMMARY OF THE INVENTION

It is an object of the present invention to provide anecomonical-non-precious-metal catalyst that capitalize on carbon nanotubes. The carbon nanotubes are made of mantle peridotite carbon mineralization based activated carbon.

The product of air pollution treatment that target pollutants such as carbon dioxide ($CO_2$) in air that uses the highly reactive rocks of mantle peridotite is natural carbon. As stated in "Precipitation" by Harrison, et al., 2013—

"Mineralization occurs naturally during weathering of silicate materials (e.g. olivine, serpentine, and wollastonite) and rocks rich in CA and Mg, particularly peridotite which composes Earth's upper mantle and basaltic lava formed by partial melting of the upper mantle."

The carbon mineralization mantle peridotite is the peridotite carbon mineralization based is then the based activated carbon for the development of carbon nanotubes.

The economical non-precious metal catalyst that capitalize on carbon nanotubes doesn't use precious metals such as platinum, is based on nitrogen-containing carbon nanotubes that does not require the tedious, toxic, and costly processing that is usually required when converting such materials for catalytic use.

The catalyst that is made from nitrogen-doped carbon-nanotubes could be used in lithium-air batteries in which can store up to 10 times as much energy as lithium-ion batteries that could power electric vehicles.

Carbon nanotubes demonstrated the potential for being used as electrical conductor to replace conventional conductive materials such as copper and aluminum. CNT conductors are extremely lightweight, corrosive-resistive, and mechanically strong while being potentially cost-effective when compared to other conventional conductive materials.

The peridotite carbon mineralization based activated carbon nanotubes is applicable to and useful for better and low cost electrodes for fuel cells, carbon nanotubes in anodes for li-ion batteries, carbon nanotubes to epoxy composites in stronger/stiffer components of windmill blades or aircraft components, carbon nanotubes in ink, carbon fibers (baseball bats, golf clubs, airplane body, car panels, any situation where metal can be replaced by carbon fiber), carbon fiber reinforce plastics or thermoplastic, car bon fabrics (twill), carbon fiber tapes, tow and sleeves, carbon nanotubes for computer chips, and carbon nanotubes mirrors for lightweight telescopes in cube sats.

DETAILED DESCRIPTION OF THE INVENTION

Figure 1:
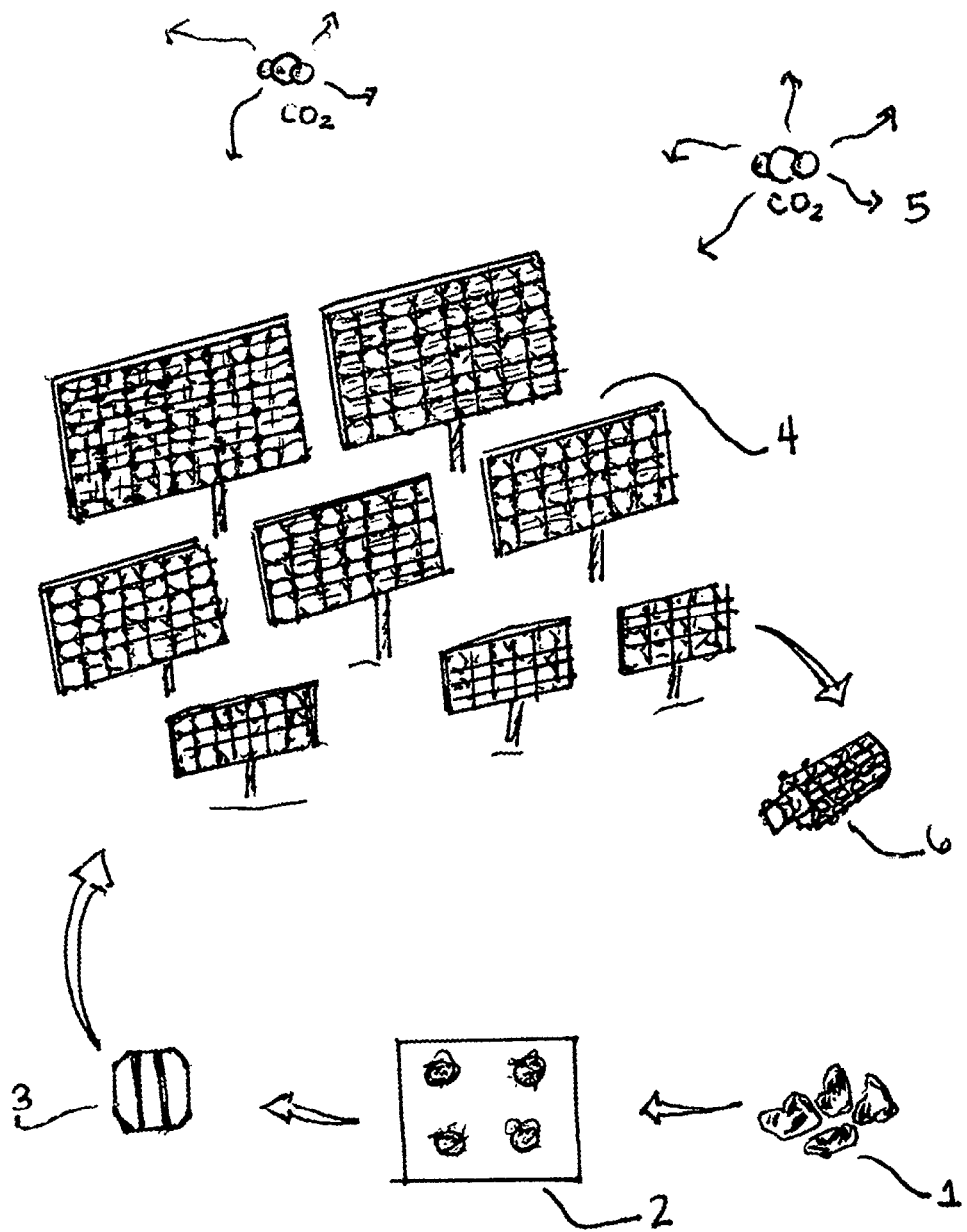
FIG. 1 shows peridotite rocks (1), ground peridotite rocks (2), a peridotite glass cell (3), peridotite photovoltaic glass panels that capture $CO_2$ in air (4), carbon dioxide ($CO_2$) (5), and carbon nanotubes (6).
Figure 2:
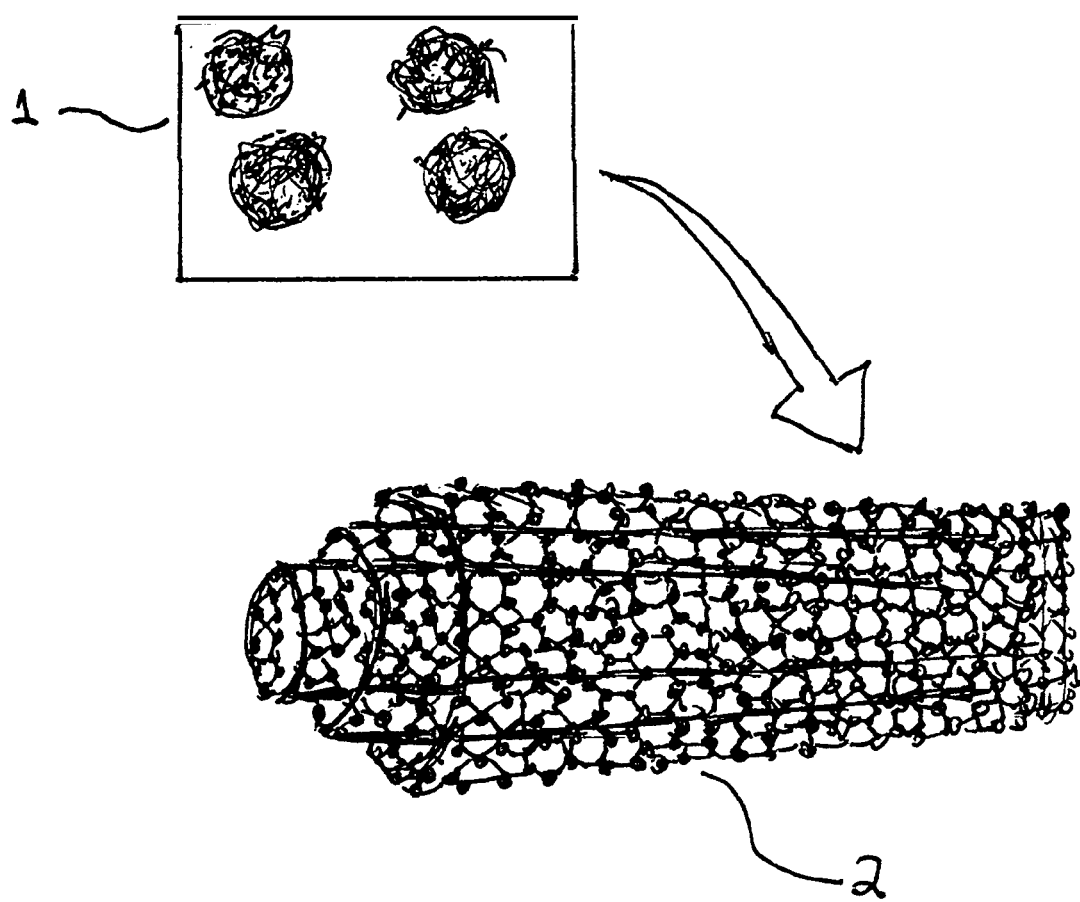
FIG. 2 shows mantle peridotite carbon mineralization based carbon (1) and peridotite carbon nanotubes (2).
Figure 3:
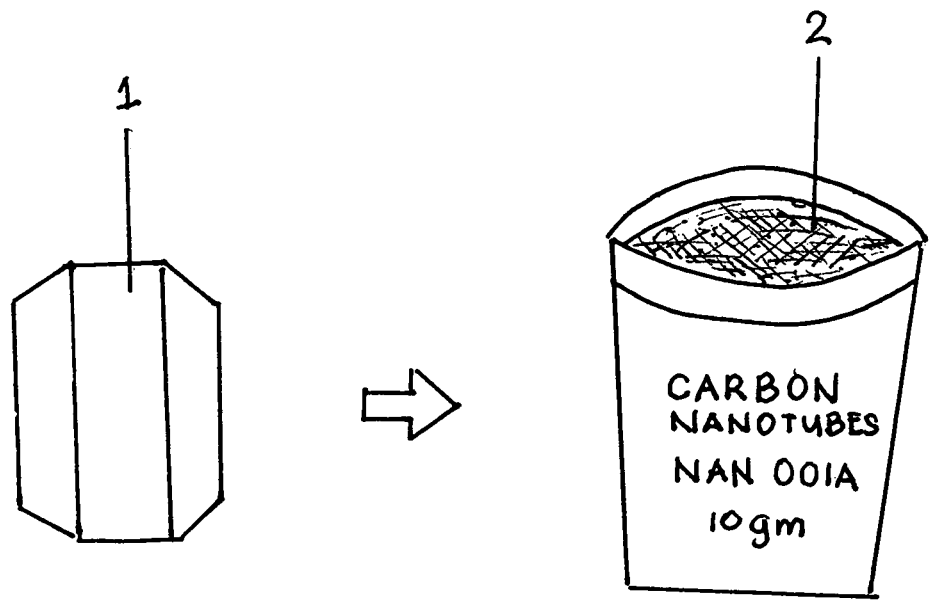
FIG. 3 shows carbon nanotubes inside a fuel cell ion battery.
Figure 4:
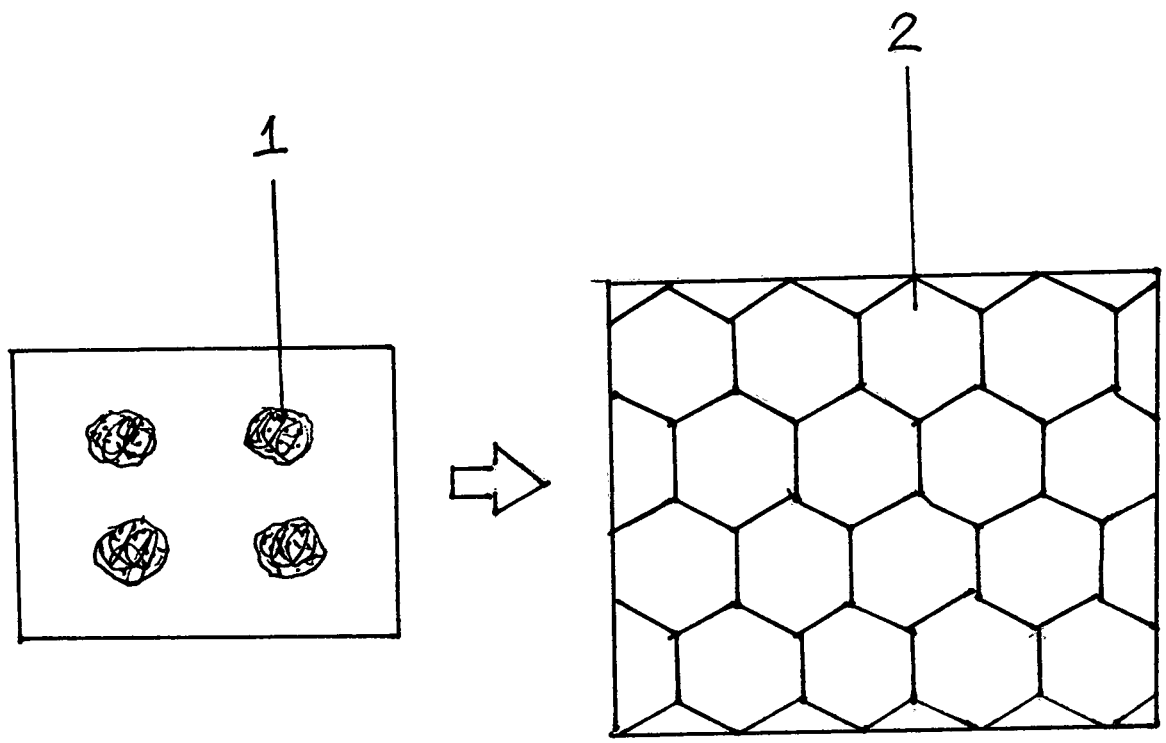
FIG. 4 shows carbon ink.
Figure 5:
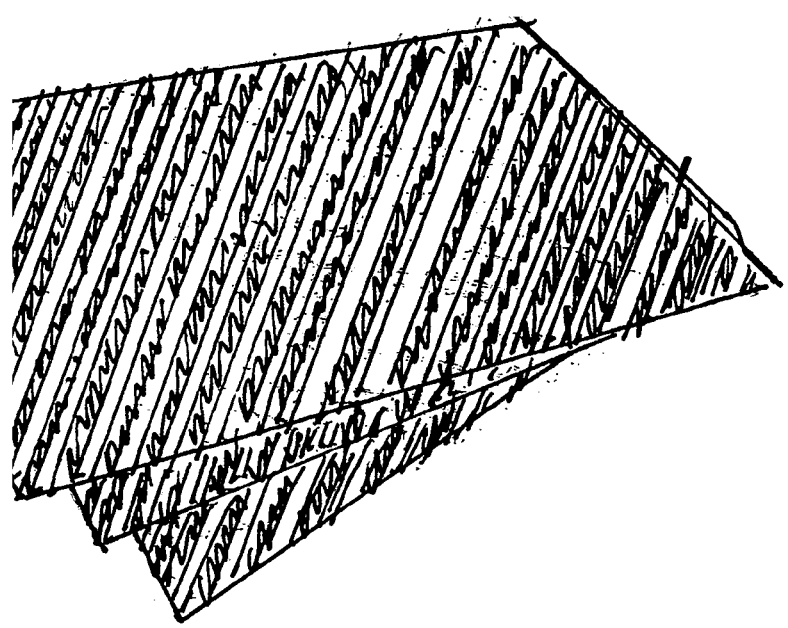
FIG. 5 shows carbon nanotubes in carbon fabric.
Figure 6:
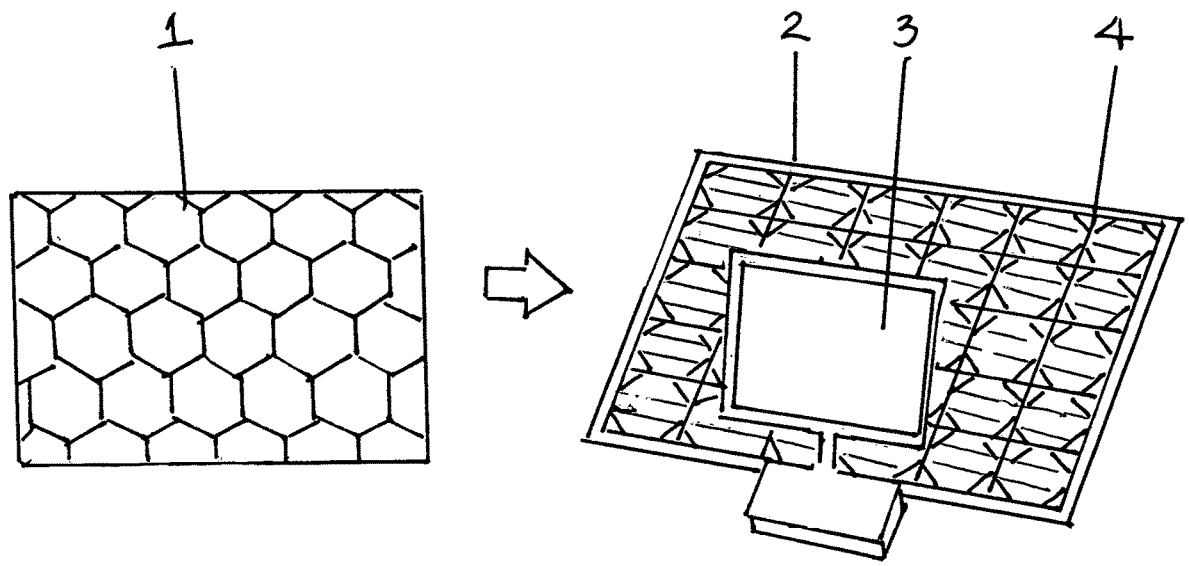
FIG. 6 shows carbon nanotubes in computer chips or computer chips made with carbon nanotubes.
Figure 7:
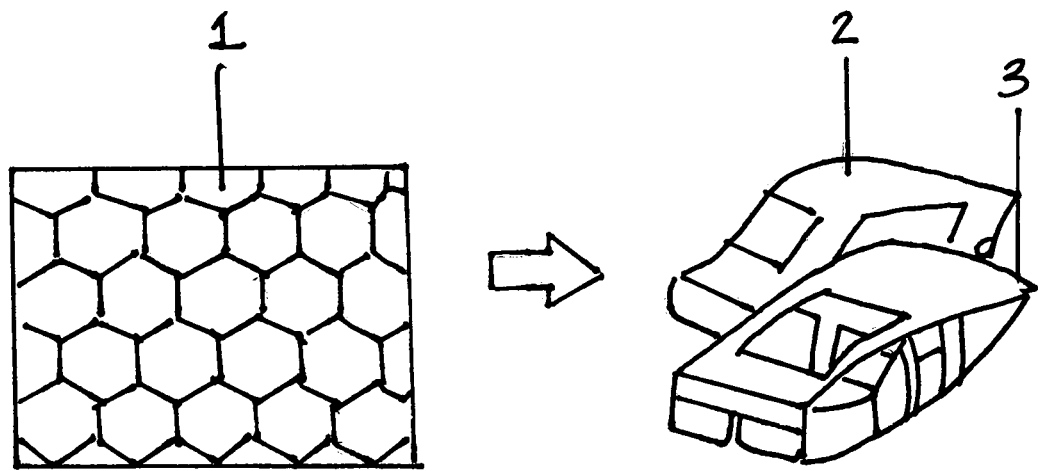
FIG. 7 shows a carbon glass window lifting panel.
Figure 8:
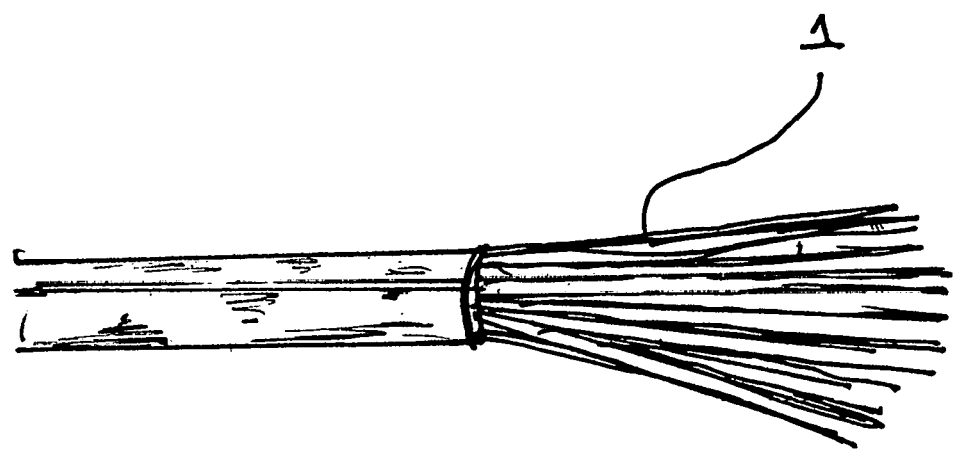
FIG. 8 shows carbon flex wires.

A nanostructured-carbon-base material made of mantle peridotite carbon mineralization based activated carbon nanotubes. The mantle peridotite carbon nanotubes is the product of air pollution treatment that target pollutants such as carbon dioxide ($CO_2$) in air using the highly reactive rock fragments of peridotite that is rich in CA and Mg. These fragments of rocks of peridotite are grinded and melted to form glass cells similar to photovoltaic cell (solar panel) and attached then to the rotor tower blades that capture $CO_2$ in air while the blades are rotating or a photovoltaic panel is made out of peridotite glass cells that can be installed in the environment to capture the $CO_2$ in air. The product of $CO_2$ sequestration using mantle peridotite glass cells is natural carbon. The carbon nanotubes of mantle peridotite is from the peridotite carbon mineralization based activated carbon.

The peridotite carbon nanotubes is efficient and reliable to use for better and low cost electrodes for li-ion batteries, carbon nanotubes to epoxy composites in stronger/stiffer components of windmill blades or aircraft components, carbon nanotubes ink, carbon fibers (baseball bats, golf clubs, airplane body, car panels, any structure where metal can be replaced by carbon fiber, carbon fiber reinforce plastics or thermoplastics, carbon fibers (twill), carbon fiber tapes, tow and sleeves, carbon nanotubes for computer chips, and carbon nanotubes mirrors for lightweight telescopes in cube sats.

As stated, nanotechnology can change the properties of many materials. This ranges from increasing the strength of materials to increasing the reactivity of materials. The new material which is the carbon nanotubes made from mantle peridotite carbon mineralization based activated carbon is an economical non-precious metal catalyst capitalizes on carbon nanotubes.

What is claimed:

1. A method for forming carbon nanotubes, comprising:
   grinding, melting and forming raw mantle peridotite into glass cells;
   exposing the glass cells to air to capture carbon dioxide in the air to convert the glass cells into mineralized carbon; and
   processing the mineralized carbon into the carbon nanotubes.

2. The method of claim 1, wherein the raw mantle peridotite is formed from peridotite rock.

3. The method of claim 1, wherein the glass cells are attached to rotor tower blades that capture the carbon dioxide in the air while the rotor tower blades are rotating.

* * * * *